United States Patent
Marra

(10) Patent No.: US 7,836,751 B2
(45) Date of Patent: Nov. 23, 2010

(54) ULTRA FINE PARTICLE SENSOR

(75) Inventor: Johan Marra, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 281 days.

(21) Appl. No.: 11/993,598

(22) PCT Filed: Jun. 26, 2006

(86) PCT No.: PCT/IB2006/052075
§ 371 (c)(1),
(2), (4) Date: Dec. 21, 2007

(87) PCT Pub. No.: WO2007/000710
PCT Pub. Date: Jan. 4, 2007

(65) Prior Publication Data
US 2010/0043527 A1    Feb. 25, 2010

(30) Foreign Application Priority Data
Jun. 28, 2005  (EP) .................................. 05105741

(51) Int. Cl.
G01N 37/00   (2006.01)
(52) U.S. Cl. .................................... 73/28.02
(58) Field of Classification Search ................. 73/28.02
See application file for complete search history.

(56) References Cited

U.S. PATENT DOCUMENTS

| | | | |
|---|---|---|---|
| 3,178,930 A | | 4/1965 | Moore et al. |
| 3,526,828 A | | 9/1970 | Whitby |
| 4,473,296 A | * | 9/1984 | Shofner et al. ............. 356/336 |
| 5,072,626 A | | 12/1991 | Ensor et al. |
| 2004/0089156 A1 | * | 5/2004 | Gartstein et al. ................ 96/53 |

FOREIGN PATENT DOCUMENTS

EP    0404093 A2    12/1990

(Continued)

OTHER PUBLICATIONS

D. B. Kittelson, et al: On-Road Exposure to Highway Aerosols. 1. Aerosol and Gas Measurements, vol. 16, No. 1 Journal, 2004, pp. 31-39.

(Continued)

*Primary Examiner*—David A. Rogers
*Assistant Examiner*—Rodney T Frank

(57) ABSTRACT

The invention relates to an ultra fine particle sensor (1) for sensing airborne particles with a diameter in a range of approximately 1-500 nm. The sensor comprises an air inlet (2) for entry of a flow of ultra fine particles and a concentration variation section (4) capable of causing a variation of the concentration of ultra fine particles between at least a first concentration level and a second concentration level during at least one time interval. A particle sensing section (5) is provided capable of producing a measurement signal (I) varying in dependence of said variation between said first concentration level and said second concentration level. An evaluation unit (6) is provided capable of deriving data relating to said ultra fine particles form said varying measurement signal. As a result of the applied variation in the concentration level, data can be obtained from the resulting variation of the measurement signal which relate to the length concentration and number concentration of airborne ultra fine particles per unit volume.

19 Claims, 7 Drawing Sheets

FOREIGN PATENT DOCUMENTS

| | | |
|---|---|---|
| EP | 0685727 A1 | 12/1995 |
| EP | 1014075 A1 | 6/2000 |
| WO | 9832001 A1 | 7/1998 |
| WO | 2006016346 A1 | 2/2006 |

OTHER PUBLICATIONS

Wang Shih Chen, et al: Scanning Electrical Mobility Spectrometer, Aerosol Science and Technology, Aug. 1990, vol. 13, No. 2, pp. 230-240.

* cited by examiner

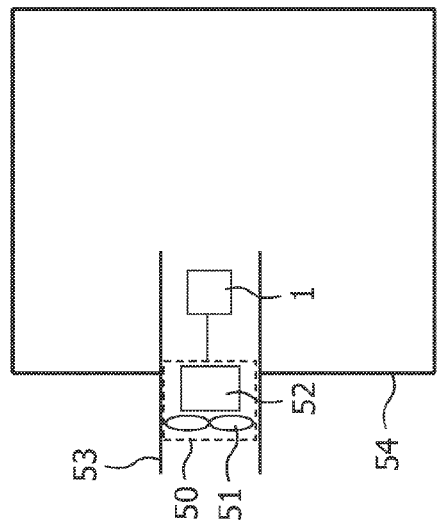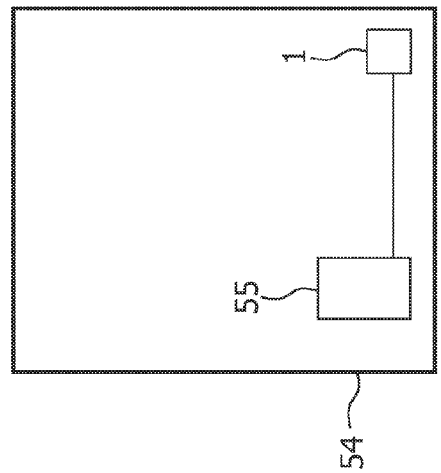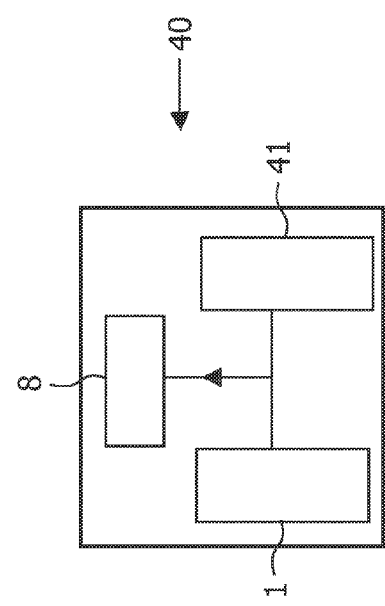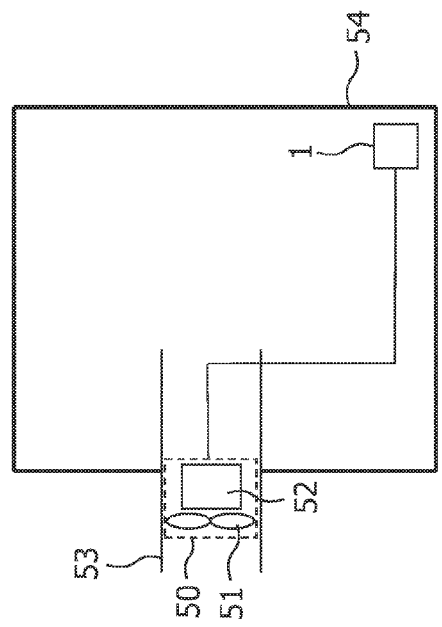

ULTRA FINE PARTICLE SENSOR

FIELD OF THE INVENTION

The invention relates to an ultra fine particle sensor and an air handling system comprising such an ultra fine particle sensor. More specifically, the invention relates to an ultra fine particle sensor for sensing airborne particles with a diameter in a range of approximately 1-500 nm, preferably 5-300 nm, more preferably 10 to 300 nm or still more preferably 20 to 300 nm

BACKGROUND OF THE INVENTION

During the past ten years, it has become increasingly clear that the inhalation of airborne combustion-related ultra fine particles (UFPs) presents a significant health-hazard to humans, owing to the fact that these particles tend to deposit on and eventually encapsulate in the lung tissue. Such UFPs comprise both solid particles and liquid-like particles. A significant part of the combustion-related solid particles is composed of soot particles that comprise or largely consist of unburned elemental carbon. A smaller part of the combustion-related solid particles is composed of inorganic ashes. Ultrafine combustion-related liquid-like particles are typically composed of more-or-less volatile hydrocarbon/$H_2SO_4$/$H_2O$ material together with small amounts of inorganic species. Combustion-related UFPs measure between approximately 5 nm and 500 nm in diameter (most particles measuring less than 200-300 nm in diameter), and normally comprise or are at least partially covered with carcinogenic polycyclic aromatic hydrocarbons (PAHs) and other volatile organic compounds (VOCs). These UFPs are emitted into air from the exhaust of combustion sources such as automobile traffic and other local combustion sources and are formed as the result of an incomplete combustion process. In particular diesel motors are notorious for emitting large amounts of soot particles and other UFPs into air.

Apart from the neighborhood of industrial combustion sources and other stationary combustion sources, the concentration of combustion-related UFPs, hereafter simply referred to as UFPs, in the western world is generally highest on or near locations where motorized traffic is present. Very high local concentrations may be encountered particularly in tunnels, traffic intersections and/or in traffic queues under conditions of limited ventilation and/or windspeed. There is increasing evidence that the impact of these UFPs on human health is more significant than that of the common gaseous exhaust pollutants (CO, $NO_x$, $SO_2$, VOCs) emitted by combustion motors. The local air pollution is thus to an important extent correlated with the local UFP concentration. In addition, the local UFP concentration is to a large extent correlated with the local concentrations of the common gaseous exhaust pollutants because they all originate from the same pollution sources.

In the prior art, the seriousness of the airborne particle pollution level is primarily established in terms of the airborne particle mass concentration associated with in particular those airborne particles that are respirable, i.e. that can reach and deposit into the alveolar region of the lungs. Since all airborne particles with $d_p \leq 10$ μm are respirable, the total respirable particle mass $M_{total}$ is considered to be a relevant parameter, $M_{total}$ being defined as $$M_{total} = \int_{dp=0}^{dp=10\,\mu m} \rho_p \frac{\pi d_p^3}{6} \frac{dN(d_p)}{d\ln d_p} d\ln d_p$$

wherein $\rho_p$ is the particle density, and wherein $dN(d_p)/d \ln d_p$ denotes the particle size distribution, $dN(d_p)$ denoting the number concentration of particles that have a diameter $d_p$. The integral is taken over the entire range of respirable particle diameters $d_p$, in practice up to $d_p=10$ μm (being the upper aerodynamic size limit for respirable particles). The respirable particle mass concentration $M_{total}$ can e.g. be measured by light scattering and/or by particle sampling/weighing.

It has been found that $M_{total}$ is in general mainly derived from particles with $d_p$>300-500 nm, even if these particles only have a very small number concentration, i.e. the number of particles per unit volume. The smaller particles do not substantially contribute to $M_{total}$ in spite of the circumstance that their number concentration is generally very high. A human health impact parameter $H_{fp}$, whose numerical value is an indication of the relative seriousness of impact on human health, taking account of respirable fine particles (FP) with $d_p$>300-500 nm can be shown to be approximately proportional with $M_{total}$ under normal environmental conditions.

In view of increasing evidence that especially UFPs with a particle diameter $d_p$ smaller than 300-500 nm are hazardous to human health, a mere measurement of only the respirable particle mass concentration $M_{total}$ would not provide reliable and/or sufficient data on the total human health impact parameter $H_{total}$ being the sum of the separate human health impact parameters for FP's and UFP's, respectively. Further, the total UFP number concentration and the number-averaged UFP diameter cannot be obtained with low-cost means.

SUMMARY OF THE INVENTION

It is an object of the invention to provide an ultra fine particle sensor that is capable of acquisition of reliable data relating to airborne UFP's.

To this end, an ultra fine particle sensor is provided for sensing airborne particles with a diameter in a range of approximately 1-500 nm, preferably 5-300 nm, comprising:

an air inlet for entry of a flow of ultra fine particles;

a concentration variation section capable of causing a variation of the concentration of ultra fine particles between at least a first concentration level and a second concentration level during at least one time interval;

a particle sensing section capable of producing a measurement signal varying in dependence of said variation between said first concentration level and said second concentration level, and an evaluation unit capable of deriving data relating to said ultra fine particles from said varying measurement signal.

It has been found that as a result of the applied variation in concentration level, data can be obtained from the resulting variation of the measurement signal which relate to the number of ultra fine particles per unit volume, i.e. the particle number concentration $N_{ufp}$. Further, the total length of the particles per unit volume, i.e. the particle length concentration $L_{ufp}$, can be inferred from this measurement signal which is approximately proportional to the human health impact parameter $H_{ufp}$ for UFP's. The combination of the data $N_{ufp}$ and $L_{ufp}$ provides valuable information on the quality of the air to which the sensor is exposed. In addition, the calculated ratio $d_{p,av}=L_{ufp}/N_{ufp}$ provides the number-averaged particle diameter $d_{p,av}$ of all airborne UFPs which helps to further characterize the airborne UFP pollution.

The embodiment of the invention as defined in claim 2 provides the advantage of an effective way of varying the concentration level and sensing the UFP's as a result of the electrical charge of the UFP's.

In the embodiment of the invention as defined in claim 3, the corona-discharge source is effective in charging different types of UFP's as mentioned above. The possible production of health-hazardous ozone may be removed by employing e.g. an activated carbon filter. The embodiment defined in claim 4 combines the corona-discharge source with a porous screen electrode enabling a further control of the charging process of the UFP's. The screen electrode allows particle charging to be accomplished at a very low electric field strength which helps to minimize particle losses during the particle charging process.

The embodiment of the invention as defined in claim 5 allows an effective charging of in particular airborne soot particles and moreover eliminates the need for applying high voltages within the ultra fine particle sensor.

It should be appreciated that the ultra fine particle sensor may also comprise more than one type of particle charging section, and may be embodied as a compound comprising more than one type or embodiment of ultra fine particle sensor.

The embodiment of the concentration variation section defined in claim 6 provides for a simple yet effective controlled variation of the concentration of charged particles in the flow reaching the particle sensing section. As an example, a series of straight or cylindrically-concentric parallel plates is employed, also referred to as a parallel plate precipitator, to which a series of voltage pulses can be applied to selected plates in order to enable a partial electric-field-induced particle precipitation on the plate surfaces to occur during at least one time interval. Parallel plates have the advantage of incurring only a negligible air pressure drop between the air inlet and the particle sensing section. Preferably, a series of non-zero voltage pulses is periodically applied, alternated with periods of zero voltage.

The embodiments of the invention as defined in claims 7 and 8 provide for a means of obtaining a varying electric signal that is proportional to the concentration of charged UFP's downstream of the concentration variation section, and which is appropriate for determining the particle number concentration $N_{ufp}$ in the air to which the sensor is exposed.

The embodiments of the invention as defined in claims 9 and 10 describe effective methods for the evaluation unit to infer the particle number concentration $N_{ufp}$ and the total length of the particles per unit volume $L_{ufp}$, respectively.

The embodiment of the invention as defined in claim 11 indicates that at the applicable air speed, a complete particle precipitation inside the concentration variation section is prevented for any group of airborne particles, possessing a diameter $d_p$, that contributes to a more-than-negligible degree to the total particle number concentration in the flow entering the ultra fine particle sensor.

The embodiment of the invention as defined in claim 12 has the advantage that coarse particles, that hardly contribute to the particle number concentration $N_{ufp}$, are removed before entering, and consequently polluting, the ultra fine particle sensor.

The embodiment of the invention as defined in claim 13 provides the advantage of enabling a regular, preferably controllable, air flow containing UFP's through the ultra fine particle sensor.

The embodiment of the invention as defined in claim 14 has the advantage of a convenient way of displaying data concerning the characteristics, e.g. the quality/pollution, of the environmental air. These data may include one or more of the following data: the particle number concentration $N_{ufp}$, the particle length concentration $L_{ufp}$, the human health impact parameter $H_{ufp}$ or data derived from these parameters such as the number-averaged particle diameter $d_{p,av}$.

The embodiment of the invention as defined in claim 15 has the advantage of a sensor capable of acquiring data relating both to UFP's and FP's.

It should be acknowledged that the above embodiments, or aspects thereof, may be combined.

The invention further relates to an air handling system comprising the ultra fine particle sensor as described above, wherein said ultra fine particle sensor has a feedback output arranged to supply a control signal capable of controlling an air cleaning unit and/or an air ventilation unit of said air handling system on the basis of said varying measurement signal.

Such an air handling system may be arranged to actively react to the measurements of the ultra fine particle sensor according to the invention, such that air conditions downstream of the air handling system can be improved if the sensor indicates a bad air quality, specified e.g. as a threshold for the particle number concentration $N_{ufp}$ and/or the particle length concentration $L_{ufp}$.

The invention will be further illustrated with reference to the attached drawings, which schematically show preferred embodiments according to the invention. It will be understood that the invention is not in any way restricted to these specific and preferred embodiments.

BRIEF DESCRIPTION OF THE DRAWINGS

In the drawings:

FIG. 7 shows a block diagram of a sensor adapted to sense ultra fine particles and fine particles according to an embodiment of the invention, and FIGS. 8A-8C show air handling systems employing an ultra fine particle sensor according to the invention.

DETAILED DESCRIPTION OF THE DRAWINGS

Figure 1:
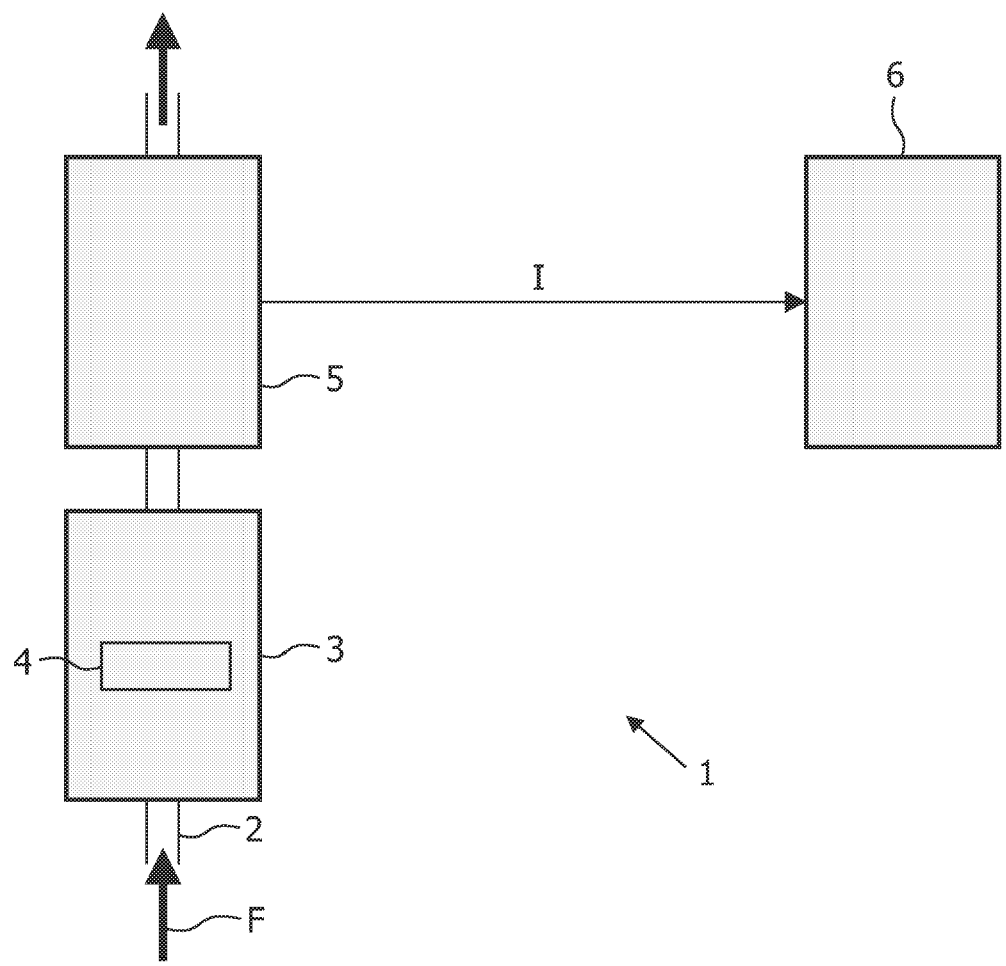
FIG. 1 shows a schematic illustration of an ultra fine particle sensor according to an embodiment of the invention.

FIG. 1 is a schematic illustration of an ultra fine particle sensor 1 having an air inlet 2 for entry of a flow F containing ultra fine particles (UFP's). The sensor 1 has a concentration variation section 3 capable of causing a variation of the concentration of UFP's. The flow variation section 3 has controllable means 4 for varying the concentration of UFP's between at least a first non-zero concentration level and a second non-zero concentration level during at least one time interval. The first non-zero concentration level may e.g. relate to a passing percentage of UFP's of approximately 100% of the UFP's entering the concentration variation section, whereas the second non-zero concentration of UFP's has a passing percentage of 70-90%. The means 4 may include an electrostatic UFP capturing means or any other means capable of (temporarily) reducing the throughput of UFP's.

A particle sensing section 5 is provided capable of producing a measurement signal I varying in dependence of said variation of the concentration of the UFP's. Finally, an evaluation unit 6 is arranged to derive data relating to said ultra fine particles from said varying measurement signal I.

Figure 2:
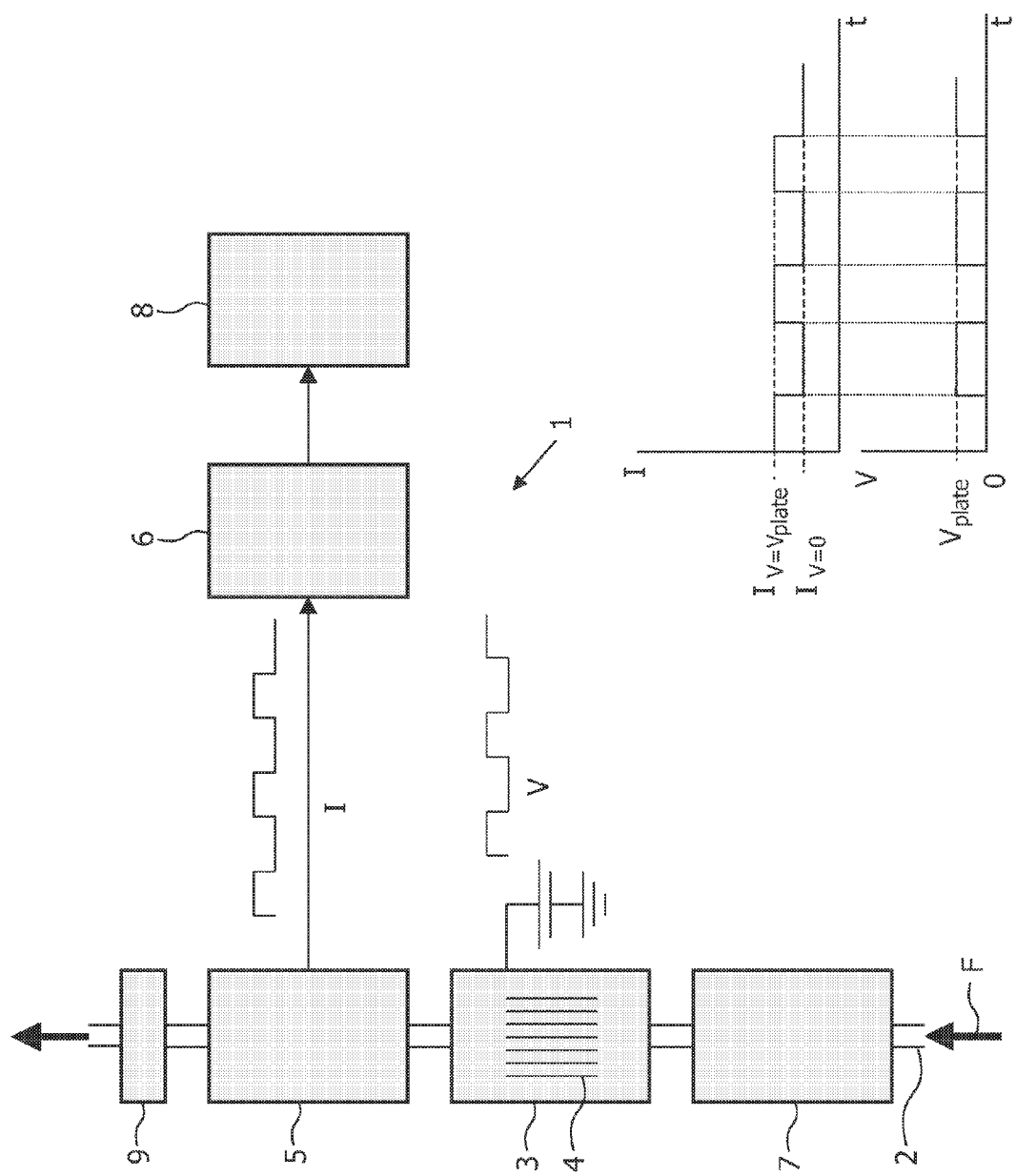
FIG. 2 shows a more specific schematic illustration of the ultra fine particle sensor of FIG. 1.

FIG. 2 shows a more specific schematic illustration of the ultra fine particle sensor of FIG. 1.

A particle charging section 7 is positioned between the air inlet 2 and the concentration variation section 3. The particle charging section 7 is capable of electrically charging at least a portion of the UFP's entering the air inlet 2. Various embodiments of particle charging sections 7 will be further discussed with reference to FIGS. 3-6.

Figure 3:
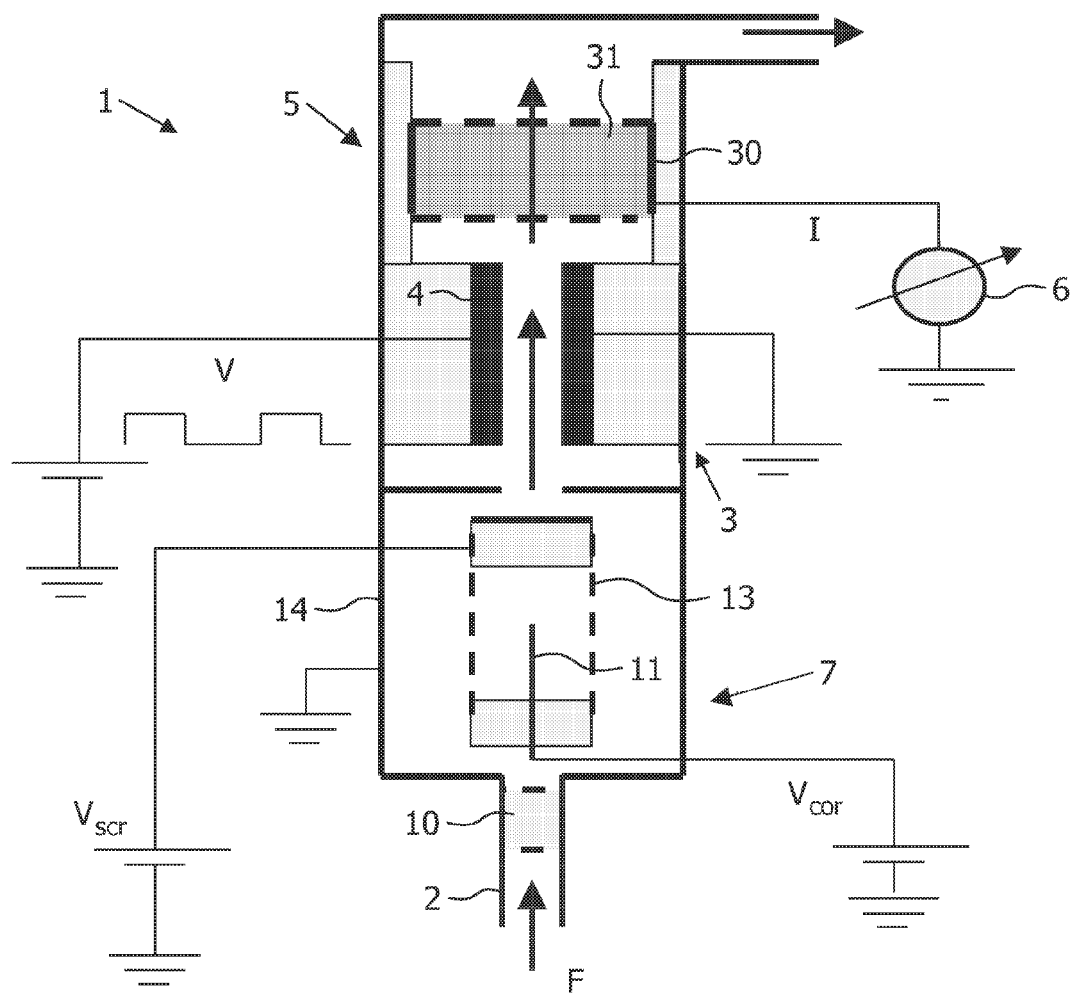
FIGS. 3-5 show schematic illustrations of ultra fine particle sensors employing a corona-discharge source.
Figure 4:
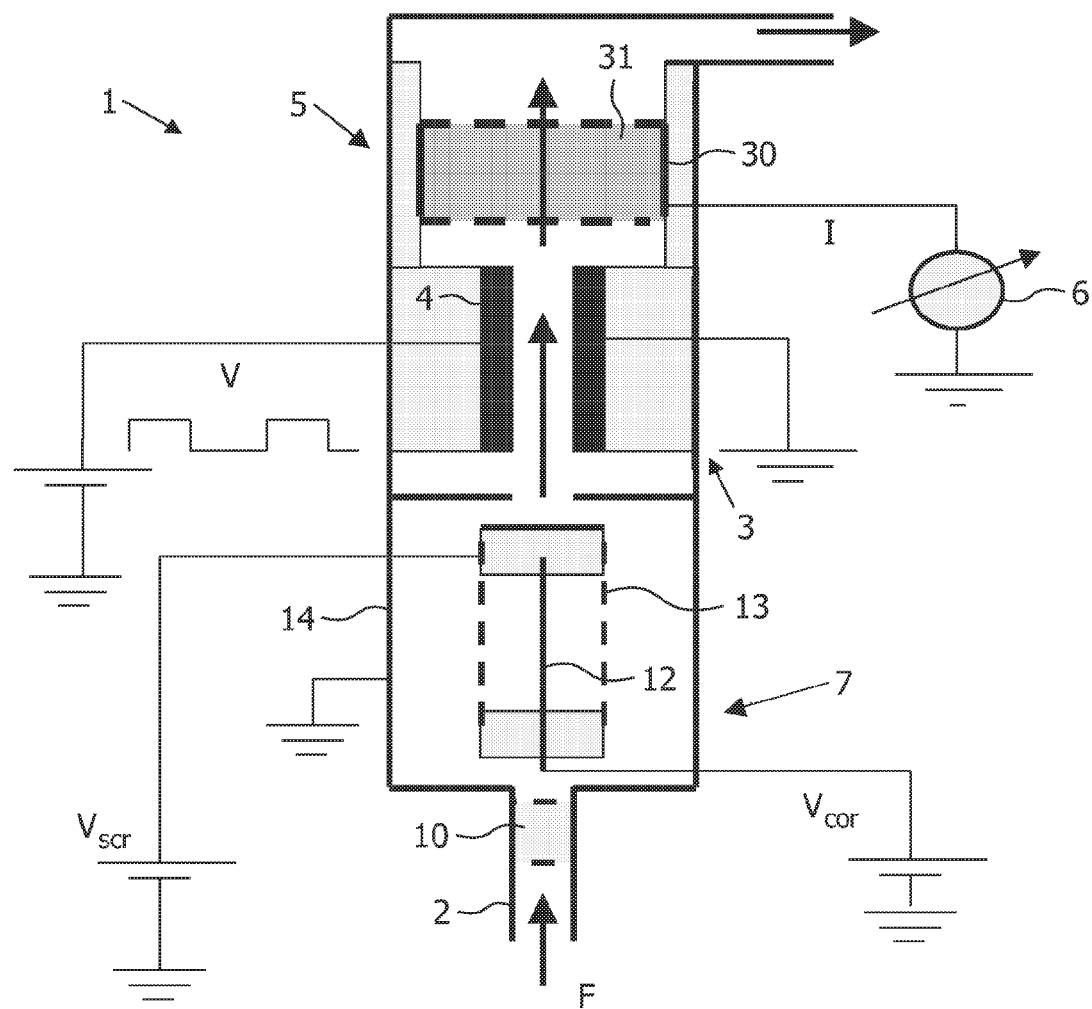
Figure 5:
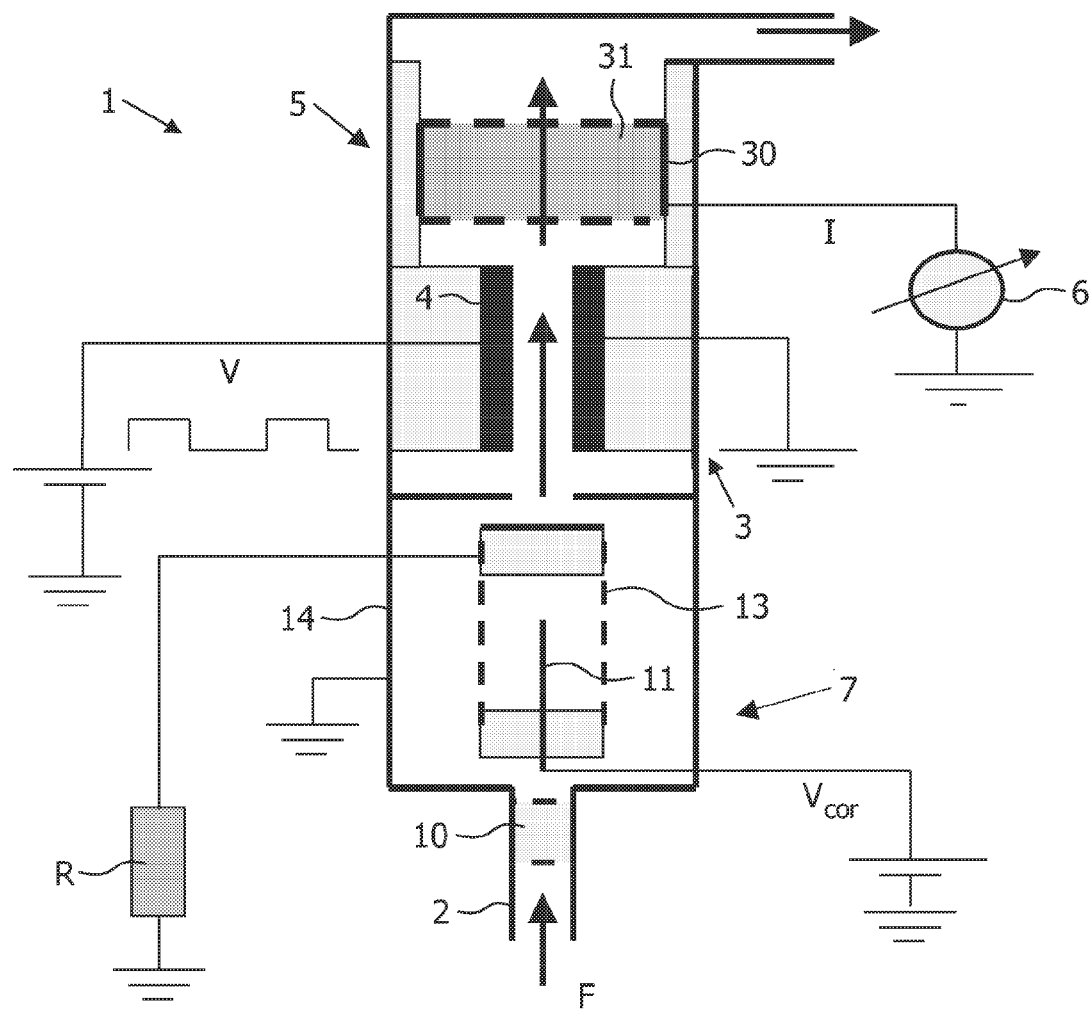

FIGS. 3-5 show schematic illustrations of ultra fine particle sensors employing a corona-discharge source of airborne ions. A needle 11 or thin wire 12 is connected to a DC voltage $V_{cor}$, sufficiently high to ionize the air in the neighborhood of the needle tip 11 or thin wire 12.

A porous screen electrode 13 is positioned around the needle 11 or thin wire 12 ion source and is set at a voltage $V_{scr}$ that is substantially smaller than $V_{cor}$ causing ions of one polarity to be drawn from the needle 11 or wire 12 towards the screen electrode. A counter-electrode 14 is positioned around the porous screen electrode 13 and is set at a counter-electrode potential that is smaller than $V_{scr}$, the counter-electrode potential preferably being set to earth potential and formed by the inner wall of the housing of the sensor 1. This enables part of the unipolar ions drawn from the needle 11 or wire 12 towards the porous screen electrode 13 to traverse the pores of the screen electrode 13 and to become drawn towards the counter-electrode 14 under the driving force of the electric field existing between the porous screen electrode 13 and the counter-electrode 14, the electric field having a strength that is preferably kept below 500 V/cm. Part of the unipolar ions that are drawn towards the counter-electrode 14 will attach themselves to the UFP's present in the received influx airflow, thereby inducing a diffusion charging of these UFP's.

In FIG. 5, the potential $V_{scr}$ is established by a grounded resistor R connected to the screen electrode.

It should be appreciated that the porous screen electrode 13 may be omitted in the sensor 1. Under these conditions of particle charging, the particle charging section 7 comprises an ion source 11, 12 and a counter-electrode 14 between which the influx airflow is received from the air inlet 2. The ion source 11, 12 produces airborne ions and is preferably embodied either as a needle-tip electrode or as a thin-wire electrode held in position between two insulators. A sufficiently high corona voltage $V_{cor}$ is imposed on the needle-tip 11 electrode or the thin-wire electrode 12 to ionize the air in the direct neighborhood of the needle tip 11 or the thin wire 12, respectively. The difference between $V_{cor}$ and the voltage imposed on the counter-electrode (preferably earth potential) induces an electric field across the airflow conduit that draws unipolar ions directly from the ion source 11, 12 towards the counter-electrode 14, thereby allowing part of the unipolar ions to attach themselves to the UFP's in the influx airflow that moves through the airflow conduit, thus enabling a particle charging to be accomplished in the presence of an electric field across the flow conduit that may or may not have a local strength exceeding 500 V/cm. The inner wall of the housing of the UFP sensor facing the ion source may be utilized as the counter-electrode 14.

Figure 6:
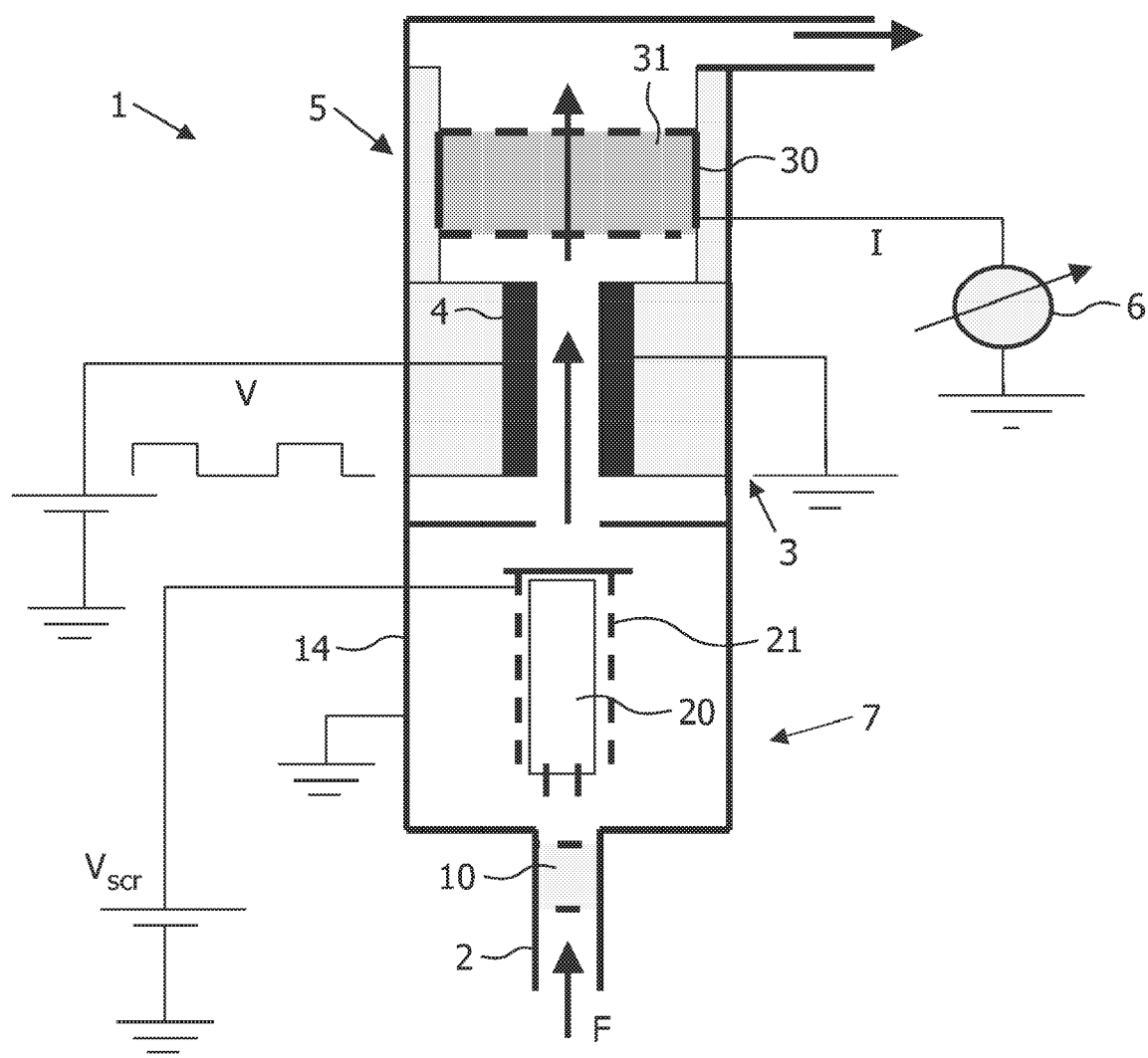
FIG. 6 shows a schematic illustration of an ultra fine particle sensor employing an ultraviolet light source.

An alternative method of charging at least a portion of the airborne UFP's is obtained by illuminating these particles by one or more light sources. This is schematically illustrated in FIG. 6. This method is especially suitable for the charging and subsequent sensing of soot particles, thus transforming the ultra fine particle sensor into a more specific soot sensor.

The particle charging section 7 in FIG. 6 comprises an UV lamp 20, e.g. a tubular low-pressure UV lamp emitting radiation that comprises a wavelength below 260 nm. Ordinary low-pressure UV lamps, such as those commonly used for disinfection purposes, are provided with a gas filling comprising mercury vapor. These UV lamps emit a peak wavelength of 253.7 nm and, in case the UV lamp is embodied as a (synthetic-) quartz lamp, an additional peak wavelength of 184.9 nm. Alternatively, the UV lamp may be a UV-excimer lamp, the radiation wavelength of which can be tuned between 170 nm and 260 nm, dependent on the nature and composition of the filling gas inside the excimer lamp. The inner wall of the sensor housing facing the UV lamp may be reflective to increase the light intensity in the flow conduit between the lamp and the sensor housing. Combustion-related UFP's that are at least partly covered with a coating of polycyclic aromatic hydrocarbon (PAH) material, which is normally the case for all soot particles, will undergo photoemission of one or more electrons when they are irradiated with UV light possessing wavelength peaks below 260 nm, which makes these particles to become positively charged. By disposing a protective conducting gauze 21 of high porosity around the UV lamp 20, the lamp is shielded from direct exposure to the airflow through the soot sensor, thereby avoiding a gradual contamination of the lamp surfaces through depositing UFP's from air, which would otherwise reduce the light output from the lamp in the course of time.

In addition, it is advantageous to impose a small DC or AC voltage of $U_0$=about 5-10 V on this gauze 21 and to earth the inner wall of the sensor 1 so that a small electrostatic field exists across the flow conduit between the gauze 21 and the inner wall. This electric field promotes the rapid removal of photo-emitted electrons and negative ions from the air while hardly affecting the transit of the positively charged soot particles towards the concentration variation section 3 (because of the much higher electrophoretic mobility of electrons and ions). The charged (and remaining uncharged) soot particles subsequently enter the concentration variation section 3 of the sensor 1. It is furthermore advantageous to provide the surfaces of the gauze 21 and the surface of the inner wall of the sensor facing the gauze with a thin non-metallic coating layer that prevents the photoemission of electrons from these surfaces when they are irradiated with UV light.

It should be acknowledged that the corona discharge embodiment of FIGS. 3-5 and the illumination embodiment of FIG. 6 may be combined.

Referring back to FIG. 2, as at least a portion of the UFP's is charged in the particle charging section 7, the variation of the concentration of UFP's in the concentration variation section 3 can be accomplished electrostatically. In particular, the means 4 of the concentration variation section 3 may be constructed as a series of straight or cylindrical-concentric parallel plates, at least one of them capable of receiving a periodic series of voltage pulses $V_{plate}$. The plates 4 are alternately connected to earth potential and to the voltage $V_{plate}$, the parallel plates being positioned side-by-side with respect to each other each extending in a plane substantially parallel to the direction of the air flow. The voltage pulses preferable alternate between a voltage V=0 Volts associated with the first concentration level and $V=V_{plate}$ associated with the second concentration level. The second concentration level is below the first concentration level since a number of charged UFP's precipitate onto the surface(s) of at least one of the plates 4 under the influence of the electrostatic field existing between adjacent plates when the voltage $V_{plate}$ is applied. $V_{plate}$ is chosen such that, at the pertaining air speed through this section 3, only a controlled partial particle precipitation occurs for all classes of equally sized charged particles of any size below $d_p$=500 nm, preferably 300 nm, that contribute to the total particle number concentration to a non-negligible degree. This generally means that at most about 95% of all charged ultra fine particles sized between approximately 10 and 20 nm in diameter should be removed from the airflow by electrostatic precipitation inside the concentration variation section 3 when the voltage $V_{plate}$ is applied. Larger particles are removed in relatively lesser degrees because the extent of particle precipitation inside the concentration variation section diminishes at increasing particle sizes, at least when these particles are charged with diffusion charging. Once particles are precipitated onto a plate surface, they become immobilized and are unable to dislodge themselves from the plate surface when the voltage $V_{plate}$ is subsequently reduced to zero.

The charged UFP's passing the concentration variation section 3 are subsequently received in the particle sensing section 5 that captures substantially all of the received UFP's. In the embodiments shown in FIGS. 3-6, a Faraday cage 30 causing all charged UFP's to deposit on the fibers of a dust filter 31 inside the Faraday cage 30 is employed. The Faraday cage 30 is held at a constant electric potential, for example by connecting it via a sensitive current meter to a common potential, preferably earth potential at the side of the evaluation unit 6. The constant electric potential of the Faraday cage 30 induces an electric current I towards the Faraday cage that compensates for the charge that accumulates inside the filter 31 disposed in the Faraday cage 30 when charged UFPs are trapped inside the dust filter 31. This electric current I constitutes the sensor signal and is equal to the charge accumulated per unit time inside the Faraday cage 30. The measuring current I, varying as a result of the varied concentration of charged UFP's through the concentration variation section 3 between $I_{V=0}$ and $I_{V=Vplate}$ is obtained and fed to the evaluation unit 6.

In case of corona charging, shown in FIGS. 3-5, the charge of the UFP's is determined by the particle diameter $d_p$, the average ion concentration $N_{ion}$ in the flow-conduit space between the screen electrode 13 and the earthed inner wall of housing of the sensor 1 and the average time of residence t of the UFP's in the charging region. It has been found that the particle charge depends on the parameters $d_p$ and the product $N_{ion} t$.

It has further been found that for corona charging, in case V=0 in the concentration variation section 3, a current $I_{V=0}$ can be recorded by the evaluation unit 6 connected to the Faraday cage 30 with a particle filter 31, that is proportional to the total length concentration $L_{ufp}$ of all UFP's. Thus, $$I_{V=0} \propto L_{ufp} = \int_{dp=0}^{dp=500\ nm} d_p \frac{dN_{ufp}}{d\ln d_p} d\ln d_p$$

As a matter of fact, also airborne particles larger than 500 nm contribute to $I_{V=0}$, and thus to $L_{ufp}$, however their contribution to $L_{ufp}$ is generally much smaller than the contribution of particles smaller than 500 nm. As $L_{ufp}$ is approximately proportional to the UFP-associated human health impact parameter $H_{ufp}$, given by $$H_{ufp} \approx Const_1 \int_{dp=10\ nm}^{dp=500\ nm} d_p^{1.5} \frac{dN_{ufp}}{d\ln(d_p)} d\ln(d_p)$$

with $Const_1$ a constant parameter depending on the physical composition of the particles, it follows that to a good approximation, $$H_{ufp} \propto I_{V=0}$$

The $d_p^{1.5}$ dependency in the expression for $H_{ufp}$ is obtained from a multiplication of the relative health impact of deposited particles (proportional to their surface area ($\sim d_p^2$)) with the deposition efficiency of these particles inside the lungs (approximately proportional with $d_p^{-0.5}$). Preferably, the source of the airborne UFPs should be known (e.g. automobile traffic) in order to determine a reliable proportionality factor between $I_{V=0}$ and $H_{ufp}$. Accordingly, data is obtained about the relative health impact $H_{ufp}$ of the UFP-polluted air.

In case V=$V_{plate} \neq 0$, part of the charged UFP's will precipitate inside the concentration variation section 6, thus yielding a current $I_{V=Vplate} < I_{V=0}$. It has been found that $$N_{ufp} \propto (I_{V=0} - I_{V=Vplate})$$

thus yielding the total UFP particle number concentration $N_{ufp}$ from a recording of the difference between two current levels at the evaluation unit 6, and a proportionality factor that depends on the degree of UFP charging and the airflow through the ultra fine particle sensor. Because $N_{ufp}$ will generally be time-dependent, it is appropriate to provide a block-shaped $V_{plate}$ to the precipitation section 3 with a frequency that is below 1 Hz. The concentration $N_{ufp}$ can then also be recorded as a function of time.

When the particle charging is performed by illumination, shown in FIG. 6, substantially only airborne soot particles are charged through irradiation with UV light possessing a sufficiently low wavelength. In case the induced photo-electric particle charge is brought to saturation (through the application of a sufficiently high irradiation intensity and/or a sufficiently long particle residence time in the UV light), it has been found experimentally that, at V=0, the recorded Faraday cage current $I_{saturation,V=0}$ becomes proportional to the total length concentration $L_{soot}$ of the soot particles. Thus $$I_{saturation,V=0} \propto L_{soot} = \int_{dp=0}^{dp=500\ nm} d_p \frac{dN_{soot}}{d\ln d_p} d\ln d_p$$

The soot-related health-impact parameter $H_{soot}$ for ultra fine soot particles follows from $$H_{soot} \approx Const_2 \int_{dp=10\ nm}^{dp=500\ nm} d_p^{1.5} \frac{dN_{soot}}{d\ln d_p} d\ln d_p$$

with $Const_2$ a constant parameter, resulting to a reasonable approximation in the proportionality relation $$H_{soot} \propto I_{saturation,V=0}$$

The soot particle number concentration $N_{soot}$ can now approximately be determined at the evaluation unit 6 from $$N_{soot} \propto (I_{saturation,V=0} - I_{saturation,V=Vplate})$$

thus yielding the total soot particle number concentration $N_{ufp}$ from a recording of the difference between two current levels at the evaluation unit 6 and a proportionality factor, which can either be determined experimentally or inferred theoretically.

An even more accurate estimate of $H_{soot}$ can be made by ensuring the photo-charging of the soot particles to remain somewhat below photo-electric saturation. The photo-electric particle charge then becomes proportional to $d_p^f$ with the exponent f falling within the range 1.0-2.0 (for fully saturated photo-charging f=1, for fully non-saturated photo-charging f=2). By carefully controlling the exposure of the airborne soot particles to UV light, it then becomes possible to record a current $I_{V=0}$ according to $$I_{V=0} \approx Const_3 = \int_{dp=0\ nm}^{dp=500\ nm} d_p^{1.5} \frac{dN_{soot}}{d\ln d_p} d\ln d_p$$

which comprises the $d_p^{1.5}$ dependency that also occurs in the expression for $H_{soot}$ shown above. In this case, a more accurate health-impact factor can be determined $H_{soot} \propto I_{V=0}$ Evaluation results can be conveniently displayed on a display 8. Preferably, means (not shown) are provided to allow for a (manual) adjustment of the proportionality factors that relate the recorded current $I_{V=0}$ to the health-impact factors $H_{ufp}$ and/or $H_{soot}$ in order to account for different airborne ultra fine particles that have different chemical compositions and/or origins, thus differently affecting human health.

A pump or ventilator 9 is provided for maintaining a flow of air through the air inlet 2 towards the particle sensing section 5. The air inlet is further provided with a particle pre-filter 10 to avoid contamination of the sensor 1 by coarse particles.

Alternatively, airflow through the sensor may be created by establishing a difference in pressure between the sensor air inlet and the sensor air exit. Such a difference in pressure is present across the wall of an air duct. Air flow through the sensor may then be established by positioning the inlet 2 in the air duct and the air outlet outside the air duct. The amount of air flowing through the sensor depends on the average speed existing inside the air duct from which air is sampled (because this at least partly sets the pressure differential between the sensor's air inlet and air exit). The average air speed may be determined from the settings of the ventilator that sets up the air flow in the air duct. This determined air speed can then be used to interpret the measured sensor signal. This process may require calibration to accurately relate the airflow through the sensor to the settings of the ventilator that sets up the air flow through the air duct.

The zero level of the amplified sensor current (indicating no particles present) can be subject to drift, e.g. due to variations in temperature. The correct zero-level may be re-established by interrupting the sensing processing. This may, for example, be done by stopping air in take or disable particle charging inside the sensor.

The ultra fine particle sensor illustrated in FIGS. 1-6 above may be provided with heating means, such as an electrical resistor heating element, at or near its inlet section, to reduce the relative humidity of the air entering the sensor, thus reducing the risk of occurrence of electrical short-circuits and/or electrical leakage problems caused moisture condensation or by having to establish electrical fields in moisture-saturated air.

FIG. 7 shows a block diagram of a sensor 40 adapted to sense ultra fine particles and fine particles (FP's) according to an embodiment of the invention. The sensor 40 comprises a sensor 1 in either one of the embodiments discussed with reference to FIGS. 1-6 and a fine particle sensor 41. The outputs, or derivatives thereof, of both UFP sensor 1 and FP sensor 41 may be displayed on the display 8. The fine particle sensor 41 may e.g. comprise a unit for measuring the mass concentration of respirable airborne fine particles within the approximate particle size range 300 nm$\leq d_p \leq$10 μm or 500 nm$\leq d_p \leq$10 μm with light scattering methods and/or with a particle sampling/weighing procedure (e.g. using a $PM_{10}$ sampling system) known as such to the man skilled in the art.

In case both respirable FP's and UFP's occur in the air sensed by the sensor 40, one has a total health impact $H_{total}=H_{fp}+H_{ufp}$ according to $$H_{total} = H_{ufp} + H_{fp}$$

$$\approx Const_3 \int_{dp=10\ nm}^{dp=500\ nm} d_p^{1.5} \frac{dN(d_p)}{d\ln d_p} d\ln d_p +$$

$$Const_4 \int_{dp=500\ nm}^{dp=10\ \mu m} d_p^3 \frac{dN(d_p)}{d\ln d_p} d\ln d_p$$

with $Const_3$ and $Const_4$ proportionality factors.

The relative magnitude of $H_{fp}$ can be assessed with e.g. light scattering employed by the device 41. This is not possible for $H_{ufp}$ for which alternative measurement methods have been invented and discussed in the present application. As mentioned before, it is known that in particular in a traffic-polluted air, $H_{ufp}$ is likely to be more important than $H_{fp}$.

Finally, in FIGS. 8A and 8B, an air handling system 50 is displayed connected to an ultra fine particle sensor 1, 40 according to the invention. The air handling system may e.g. comprise a ventilator 51 and/or an air conditioning/cleaning system 52 to handle air introduced via a conduit 53. The sensor 1, 40 may be positioned inside the conduit 53, either upstream and/or downstream from the air handling system 50, and/or inside an enclosure 54 into which the air conduit 53 feeds air or from which air is extracted. The enclosure may e.g. relate to a vehicle or a room in a building. More than one sensor 1, 40 may be employed. The sensor(s) may control the settings and operation of the units of the air handling system 50 based on the varying measurement signal or, more specifically, on the data relating to the ultra fine particles and/or soot particles and/or respirable particles obtained from one or more of the sensor(s) 1, 40.

It should be appreciated that the sensors 1, 40 are not necessarily combined with an air handling system, but may also be a stand-alone sensor, e.g. a handheld sensor.

The ultra fine particle sensor 1, 40 according to the invention may also be coupled to a (portable) air cleaning device 55, as shown in FIG. 8C. Portable air cleaning devices are frequently used to clean indoor air in residential enclosures, such as living rooms and bedrooms, and typically comprise a ventilator and one or more air cleaning filters. The sensor 1, 40 may be positioned inside the portable air cleaner, attached to the air cleaner, or positioned away from the portable air cleaner inside the enclosure 54 wherein the air is cleaned by the portable air cleaner 55. More than one sensor 1, 40 may be employed. The sensor(s) may control the operational settings of the portable air cleaner (airflow, on/off switching) based on the varying measurement signal or, more specifically, on the data relating to the ultra fine particles and/or soot particles and/or respirable particles obtained from one or more of the sensor(s) 1, 40. The sensor(s) 1, 40 may be in a wireless communication with the air cleaning device.

In an air pollution sensor system comprising an UFP or soot sensor and an air cleaning unit, the air cleaning unit may be fitted with a bypass for bypassing the air cleaning unit, the amount of air directed to the bypass being under the control of the sensor. In case air drawn into the system is heavily polluted with ultrafine particles, the sensor may direct at least a substantial part of the air to the air cleaning unit whereas air having low levels of pollution is directed at least substantially to the bypass thus saving power by avoiding the pressure drop occurring in the cleaning unit.

The proposed sensors 1, 40 are simple and low cost and can be either used alone or in combination with each other. They require only basic cleaning maintenance and can be used for assessing the particle pollution level in both (ordinary) ambient air and in (severely) polluted air. The sensors 1, 40 may not be able to measure very low particle number concentrations such as in a clean-room environment.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

The invention claimed is:

1. An ultra fine particle sensor for sensing airborne particles with a diameter in a range of approximately 5-500 nm, comprising:
    an air inlet for entry of a flow of ultra fine particles;
    a concentration variation section capable of causing a variation of the concentration of ultra fine particles between at least a first concentration level and a second concentration level during at least one time interval;
    a particle sensing section capable of producing a measurement signal being an electric current varying between at least a first current level corresponding to the first concentration level and a second current level corresponding to the second concentration level, and
    an evaluation unit capable of deriving the particle number concentration entering the air inlet by comparing the first current level and the second current level, the particle number concentration being associated with ultra fine particles with a diameter of about 5 nm or larger, wherein the evaluation unit is further capable of deriving the particle length concentration from the first current level, the particle length concentration being associated with ultra fine particles with a diameter of about 5 nm or larger.

2. The ultra fine particle sensor according to claim 1, wherein said concentration variation section is capable of accomplishing said first concentration level and said second concentration level such that both said concentration levels remain non-zero for all ultra fine particles sized larger than about 5.

3. The ultra fine particle sensor according to claim 1, wherein said air inlet comprises a pre-filtration section capable of filtering particles with a diameter larger than approximately 5 µm.

4. The ultra fine particle sensor according to claim 1, further comprising a pump or ventilator capable of and arranged for maintaining a flow of air through said air inlet towards said particle sensing section.

5. The ultra fine particle sensor according to claim 1, further comprising a display capable of receiving and displaying data relating to said ultra fine particles from said evaluation unit.

6. The ultrafine particle sensor according to claim 5, being arranged to switch off the particle charging section for a period of time during which the measurement signal is set to zero.

7. The ultra fine particle sensor according to claim 1, being arranged to interrupt the flow of ultrafine particles for a period of time during which the measurement signal is set to zero.

8. An ultra fine particle sensor for sensing airborne particles with a diameter in a range of approximately 5-500 nm, comprising:
    an air inlet for entry of a flow of ultra fine particles;
    a concentration variation section capable of causing a variation of the concentration of ultra fine particles between at least a first concentration level and a second concentration level during at least one time interval;
    a particle sensing section capable of producing a measurement signal varying in dependence of said variation between said first concentration level and said second concentration level, and
    an evaluation unit capable of deriving data relating to said ultra fine particles from said varying measurement signal
    a particle charging section upstream from said concentration variation section, which particle charging section is capable of electrically charging at least a portion of said ultra fine particles and wherein said concentration variation section is arranged to produce a variable electric field capable of causing said variation of the concentration of charged ultra fine particles.

9. The ultra fine particle sensor according to claim 8, wherein said particle charging section comprises at least one corona-discharge source, and a counter-electrode and means for applying a first voltage to said corona-discharge source and a second voltage to said counter-electrode and wherein said corona-discharge source and counter-electrode are arranged with respect to said air inlet such that at least a portion of said ultra fine particles can be electrically charged.

10. The ultra fine particle sensor according to claim 9, wherein said particle charging section further comprises a porous screen electrode at least partly surrounding said corona-discharge source and means for applying a third voltage to said porous screen electrode.

11. The ultra fine particle sensor according to claim 8, wherein said particle charging section comprises at least one light source, capable of emitting light for electrically charging at least a portion of said ultra fine particles.

12. The ultra fine particle sensor according to claim 8, wherein said concentration variation section comprises at least one set of substantially parallel plates and means for applying a variable voltage to at least one of said plates to vary said electric field during at least one time interval.

13. The ultra fine particle sensor according to claim 8, wherein said particle sensing section comprises a particle filter capable of capturing at least a portion of said charged ultra fine particles and producing an electric current varying between at least a first current level corresponding to said first concentration level and a second current level corresponding to said second concentration level.

14. The ultra fine particle sensor according to claim 13, wherein said particle sensing section comprises a porous particle filter disposed within a Faraday cage and wherein said Faraday cage is connected to said evaluation unit for processing said electric current.

15. An ultra fine particle sensor for sensing airborne particles with a diameter in a range of approximately 5-500 nm, comprising:
an air inlet for entry of a flow of ultra fine particles;
a concentration variation section capable of causing a variation of the concentration of ultra fine particles between at least a first concentration level and a second concentration level during at least one time interval;
a particle sensing section capable of producing a measurement signal varying in dependence of said variation between said first concentration level and said second concentration level, and
an evaluation unit capable of deriving data relating to said ultra fine particles from said varying measurement signal, and
wherein said varying measurement signal is an electric current varying between at least a first current level corresponding to said first concentration level and a second current level corresponding to said second concentration level and said evaluation unit is capable of deriving the number of ultra fine particles per unit volume entering said air inlet by comparing said first current level and said second current level, said number of ultra fine particles per unit volume being associated with ultra fine particles with a diameter of about 5 nm or larger.

16. The ultra fine particle sensor according to claim 15, wherein said evaluation unit is further capable of deriving the length concentration of said ultra fine particles from said first current level, said length concentration being associated with ultra fine particles with a diameter of about 5 nm or larger.

17. The ultra fine particle sensor for sensing airborne particles with a diameter in a range of approximately 5-500 nm, comprising:
an air inlet for entry of a flow of ultra fine particles;
a concentration variation section capable of causing a variation of the concentration of ultra fine particles between at least a first concentration level and a second concentration level during at least one time interval;
a particle sensing section capable of producing a measurement signal varying in dependence of said variation between said first concentration level and said second concentration level, and
an evaluation unit capable of deriving data relating to said ultra fine particles from said varying measurement signal, and
a particle mass sensing section capable of obtaining data relating to particles having a diameter in the range of approximately 500 nm-10 µm.

18. An air handling system comprising an ultra fine particle sensor, for sensing airborne particles with a diameter in a range of approximately 5-500 nm, the ultra fine particle sensor including:
an air inlet for entry of a flow of ultra fine particles;
a concentration variation section capable of causing a variation of the concentration of ultra fine particles between at least a first concentration level and a second concentration level during at least one time interval;
a particle sensing section capable of producing a measurement signal varying in dependence of said variation between said first concentration level and said second concentration level, and
an evaluation unit capable of deriving data relating to said ultra fine particles from said varying measurement signal, and
wherein said ultra fine particle sensor has a feedback output arranged to supply a control signal capable of controlling an air conditioning/cleaning unit and/or an air ventilation unit associated with said air handling system on the basis of said varying measurement signal.

19. The air handling system according to claim 18, wherein said air conditioning/cleaning unit is a portable unit.

* * * * *